United States Patent [19]

Woods

[11] Patent Number: 5,592,698

[45] Date of Patent: Jan. 14, 1997

[54] TEAR-OFF LENS FOR TRANSPARENT EYE AND FACE SHIELD

[76] Inventor: Marlen M. Woods, 112 Gross Rd., Mesquite, Tex. 75149

[21] Appl. No.: 497,406

[22] Filed: Jun. 30, 1995

[51] Int. Cl.⁶ .................. A42B 3/00; A61F 9/02
[52] U.S. Cl. .................. 2/424; 2/434
[58] Field of Search .................. 2/434, 424, 9, 2/10, 206, 441, 443, 427, 447

[56] References Cited

U.S. PATENT DOCUMENTS

| | | | |
|---|---|---|---|
| 3,945,044 | 3/1976 | McGee et al. | 2/14 H |
| 4,044,890 | 8/1977 | Kramming | 206/493 |
| 4,047,249 | 9/1977 | Booth | 2/10 |
| 4,076,373 | 2/1978 | Moretti | 2/434 X |
| 4,138,746 | 2/1979 | Bergmann | 2/434 X |
| 4,179,756 | 12/1979 | Lucas | 2/434 |
| 4,455,689 | 6/1984 | Boyer | 2/434 |
| 4,716,601 | 1/1988 | McNeal | 2/434 |

*Primary Examiner*—Peter Nerbun
*Attorney, Agent, or Firm*—Akin, Gump, Strauss, Hauer & Feld, L.L.P.

[57] ABSTRACT

A tear-away lens for maintaining visibility through a transparent protective eye and face shield of a racing vehicle driver's helmet includes a tab portion having projections formed thereon to assist in grasping the tab portion to rapidly tear away the lens when visibility through the lens is reduced. The lenses may be stacked one on top of the other whereby they may be successively peeled or torn away from the shield as they become dirty or otherwise damaged whereby the wearer of the helmet may maintain suitable visibility through the shield. Each lens sheet except the outermost lens has its grasping tab elastically folded between adjacent sheets and disposed over a lens support on the shield.

9 Claims, 2 Drawing Sheets

5,592,698

TEAR-OFF LENS FOR TRANSPARENT EYE AND FACE SHIELD

FIELD OF THE INVENTION

The present invention pertains to a transparent auxiliary tear-off lens for racing helmet face shields and the like having an improved grasping tab or ear portion for tearing the lens away to reveal a clean undamaged lens.

BACKGROUND

Helmets used by automobile and motorcycle race drivers, for example, are typically provided with a protective transparent shield for shielding the eyes and face of the driver from dust, mud, oil and other airborne contaminants. Such shields also, of course, may protect the driver's face from exposure to air impinging on the face and eyes due to the high velocities of the race vehicle. However, the protective face shields can, in the course of a race or under practice runs of the vehicle, become quickly contaminated with mud and oil, for example, thereby reducing the driver's visibility substantially. Since the driver is usually quite preoccupied with handling the race vehicle, he or she has little time for reaching up to attempt to clean the shield by wiping a gloved hand across the shield. Moreover, the driver certainly has virtually no time to use any kind of a cloth or other cleaning member to remove dirt and other contaminants from the shield. developed which may be provided in stacked relationship on the helmet shield and torn or peeled away successively as the lenses become splattered with mud, oil or other debris from the racetrack. U.S. Pat. No. 4,138,746 to D. W. Bergmann, issued Feb. 13, 1979, describes a tear-away lens for covering the face shield of a driver's helmet. This patent, which is incorporated by reference herein, describes an arrangement wherein the helmet or shield is provided with spaced apart post-like fasteners on which are secured flexible transparent sheet-like lenses, each having a tab portion which may be grasped by the driver with one hand and rapidly peeled or torn away to expose a new lens. As each lens becomes contaminated and visibility therethrough is reduced, it is torn away to expose a clean uncontaminated lens. Plural lenses are usually stacked one on top of the other in numbers necessary to enable the driver to complete a race while preserving good visibility through the helmet shield.

Although the lens arrangement described in the Bergmann patent is useful, it has proven to be difficult to properly grasp and tear away when such action is required. Typically, a race driver has precious little time to take his hands off of the vehicle steering wheel or handlebars to grasp a tab or lobe attached to the lens to effect removal of the lens. Moreover, the driver is usually wearing relatively thick driving gloves which reduce dexterity when attempting to grasp the thin somewhat slick surfaces of the lens grasping tab portion.

Accordingly, there has been a need to improve the tear-away lenses described in the Bergmann patent and as further described herein by providing suitable means on the finger or thumb grasping tab of the lenses sheet to minimize slippage and failure of the grasping effort. It is to these ends that the present invention has been developed.

SUMMARY OF THE INVENTION

The present invention provides an improved tear-away lens for use in conjunction with eye protective face shields of race driver helmets and the like wherein each of the tear-away lenses includes a tab adapted to be grasped by the wearer of the helmet more effectively and firmly to assure that the lens can be quickly torn away and the wearer can return his or her hand to controlling a vehicle.

The invention contemplates the provision of a thin, flexible, transparent tear-away lens for use with a race driver's helmet, which lens has a tab portion having surface interruptions formed thereon which increase the surface roughness of the tab portion and provide for easier gripping action by the user to quickly tear away the lens and expose a clean lens for improved visibility.

In a preferred embodiment of the invention, the surface interruptions on the tear-away lens tab portion are provided by a plurality of projections extending from one surface of the tab portion and preferably adjacent to a hole or opening in the tab portion through which the user's finger may project during the tear-away action.

In accordance with another important aspect of the invention, tear-away lenses for use by race drivers to provide a substantially continuously clean viewing field through a helmet face shield are provided with plural rows of spaced projections, some of which may perforate the lens grasping tab to increase the roughness of the surface of the tab and enable a gloved driver to firmly grasp the tear-away lens to remove it from its working position.

Those skilled in the art will further appreciate the above-mentioned superior features of the invention together with other important aspects thereof upon reading the detailed description which follows in conjunction with the drawing.

DESCRIPTION OF A PREFERRED EMBODIMENT

Figure 1:
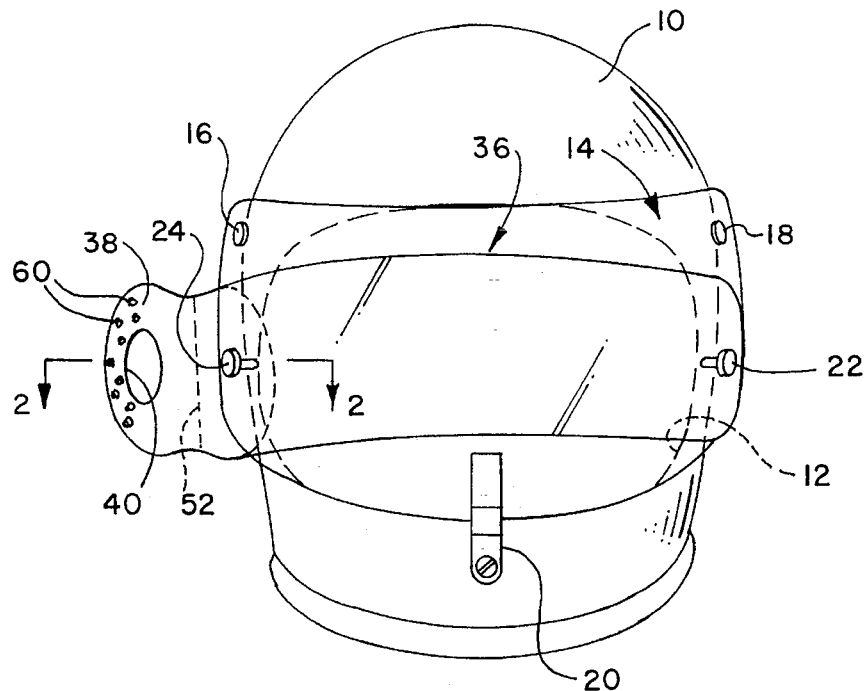
FIG. 1 is a front elevation of a conventional helmet used by race vehicle drivers adapted to include the tear-away lens of the present invention.

In the description which follows, like parts are marked throughout the specification and drawing with the same reference numerals, respectively. The drawing figures are not necessarily to scale in the interest of clarity and conciseness.

Figure 2:
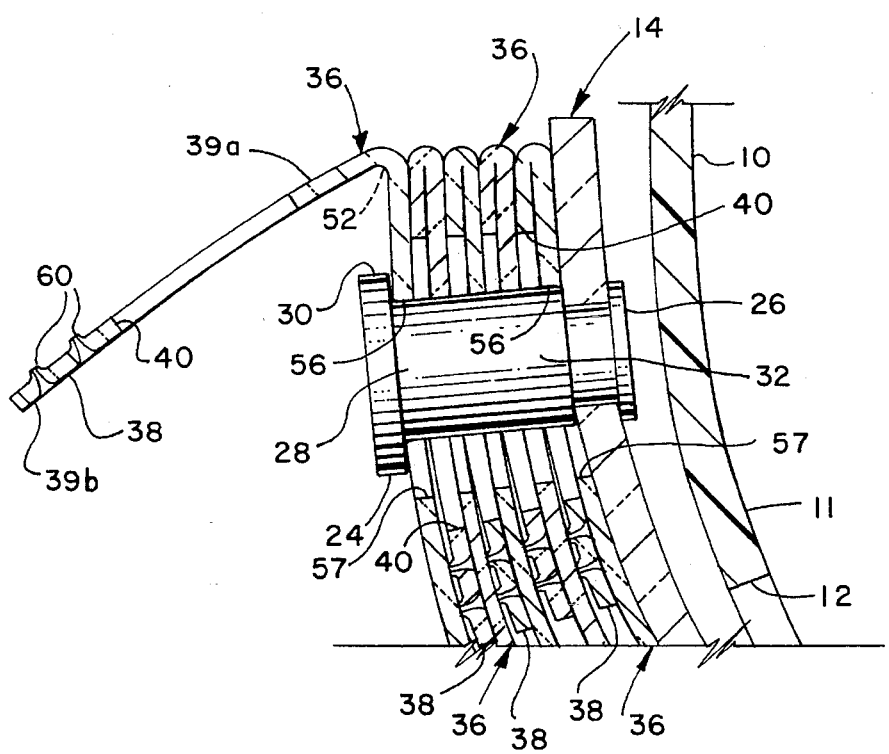
FIG. 2 is a section view taken generally along the line 2—2 of FIG. 1.

Referring to FIG. 1, there is illustrated a conventional protective helmet 10 of a type typically worn by drivers of vehicles including racing automobiles, motorcycles and boats, for example. The helmet 10 includes a frontal opening 12 over which is disposed a transparent substantially rigid protective shield 14. The shield 14 is adapted to be secured to the helmet 10 by suitable fasteners 16 and 18 and may be latched in a closed working position by suitable latch means 20. The shield 14 is also provided with spaced apart opposed posts 22 and 24 which are secured to the shield 14 adjacent to opposite sides of the opening 12 and normally at about the eyeline of the wearer of the helmet 10. The posts 22 and 24 may comprise snap together type fasteners which, as shown in FIG. 2, by way of example, comprises a base portion 26 for the post 24 and a releasable post like snap on member 28 having a circular flange 30 and a reduced diameter hub 32. The post 24 is exemplary and other configurations of support posts may be used in conjunction with the invention.

As mentioned previously, the transparent face shield 14 is subject to being impinged by all types of particulates and fluids including mud, sand, oil, water, engine coolant, insects and other types of debris which can accumulate on and reduce visibility through the shield. To overcome this problem without requiring that the helmet wearer spend a considerable amount of time attempting to clean the shield while operating a vehicle, the tear-away lens system described in U.S. Pat. No. 4,138,746 was developed to provide a solution to the face shield contamination problem. FIG. 1 shows one or more of an improved tear-away lens in accordance with the invention supported on the shield 14 and generally designated by the numeral 36. The tear-away lens 36 each, preferably, comprise a relatively thin flexible sheet of transparent material such as smooth vinyl acetate having a thickness of about 0.20 millimeters, for example. Each lens has a foldable ear or tab portion 38 with an enlarged grasping hole 40 formed therein. Each lens 36 is basically an elongated flexible flat sheet of the aforementioned plastic having a suitable width to provide the requisite field of vision through the shield 14.

Figure 3:
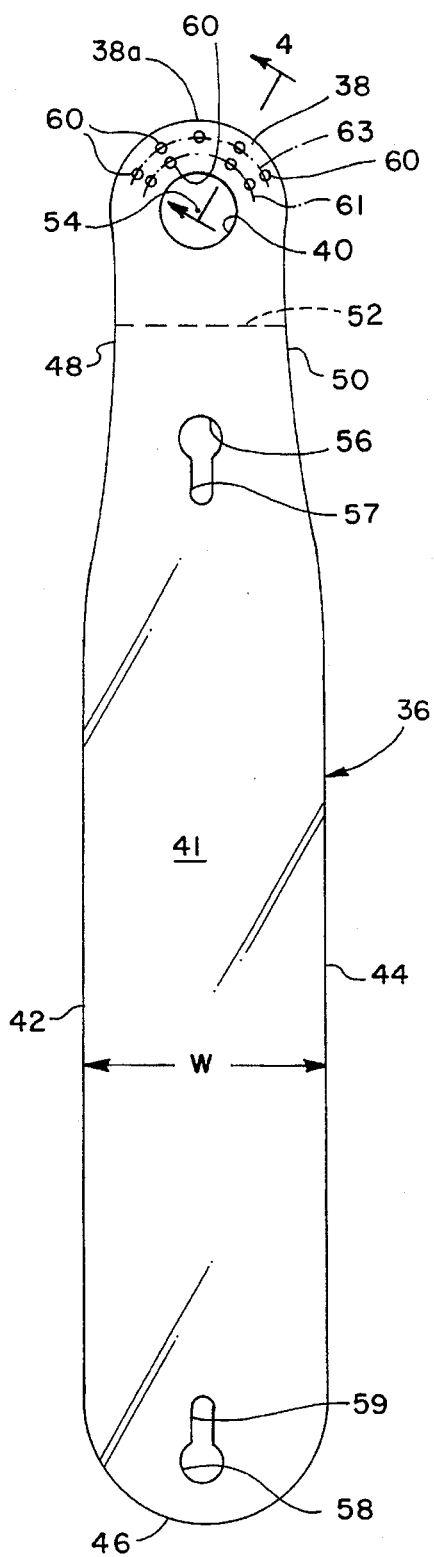
FIG. 3 is a plan view of the improved tear-away lens of the present invention.

Referring to FIG. 3, one of the lenses 36 is illustrated in plan view and includes an elongated body portion 41 delimited by opposed parallel sides 42 and 44 which terminate at one end in an arcuate end portion 46. The sides 42 and 44 extend in the opposite direction to a reduced width portion formed by shallow concave surfaces 48 and 50 adjacent an imaginary transverse fold line 52. The fold line 52 is disposed approximately half way between the center 54 of the circular hole 40 and a support post receiving hole 56 disposed on the other side of fold line 52. A second fastener or support post receiving hole 58 is spaced from the hole 56 a distance substantially equal to the circumferential distance between the posts 22 and 24. Each of the post receiving holes 56 and 58 is provided with a reduced width slot portion 57 and 59, respectively, to facilitate fastening the lens 36 to the spaced apart post fasteners 22 and 24. The diameters of the holes 56 and 58 are slightly less than the diameters of the flanges of the posts 22 and 24, such as the flange 30 illustrated for the post 24 in FIG. 2. Accordingly, when one of the lenses 36 is folded along the fold line 52, the central axes of the holes 40 and 56 are aligned with each other and the lenses 36 may be stacked one on top of the other in the manner described in the above-referenced patent, and as shown in FIG. 2. The slots 57 and 59 may be replaced by generally radially extending spaced apart slits in the body of the lens 36 extending from the respective holes 56 and 58, also in the manner described in U.S. Pat. No. 4,138,746.

As shown in FIGS. 1 and 2, the outermost lens 36, subject to being exposed to vision reducing contaminants, has its tab portion 38 projecting outwardly from the side of the helmet 10. As each tab portion of each of the stacked lenses 36 is folded over and aligned with the post receiving hole 56, that tab portion may be folded flat against the body of the lens 56 in the manner illustrated in FIG. 2. However, the outermost tab 38 will tend to assume the position illustrated in FIG. 2 due to the elastic memory of the material of which the lenses are made. Moreover, during movement, airflow along the lens 36 will tend to deflect the tab portion 38 toward the position shown in FIG. 2.

Figure 4:
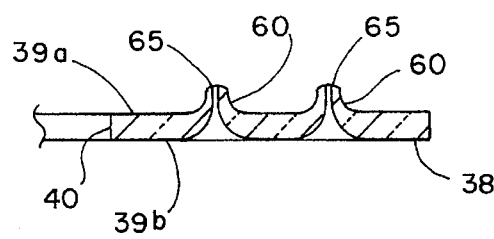
FIG. 4 is a detail section view taken generally from the line 4—4 of FIG. 3.

It has been determined that in use of the tear-away lenses described in U.S. Pat. No. 4,138,746, attempts to grasp the tab 38 to tear away a lens have met some difficulty in firmly grasping the tab and inserting a finger through the hole 40. In fact, many race vehicle drivers, including motorcycle drivers, in particular, wear rather heavy protective gloves which reduce dexterity and the ease with which the tab 38 may be grasped. Moreover, the smooth transparent plastic material of which the lenses 36 are made also tends to reduce the ease with which the tab 38 may be grasped. Accordingly, the lens 36 is provided with unique gripping enhancing means on the tab 38 formed by surface interruptions comprising a plurality of spaced apart projections 60, see FIGS. 2, 3 and 4, which interrupt one or both of the opposed surfaces 39a and 39b, FIG. 4, a sufficient amount to substantially improve the ease with which the tab 38 may be grasped by the thumb and forefinger, for example, of a person attempting to remove the outermost lens 36 from its working position to expose a clean lens underneath or to expose a clean uncontaminated shield underneath the removed lens.

The projections 60 are preferably provided in an arcuate multiple row pattern, as illustrated in FIG. 3, including a first inner arcuate row 61 of four projections and a second outer, arcuate row 63 of five projections. The rows are spaced apart between the hole 40 and the arcuate distal edge 38a of the tab 38. The projections 60 may be randomly placed or in other patterns on the tab 38 in the general area shown. The projections 60 may be formed by a suitable die or punch to create a displaced portion of the material of the lens 36 and the length of the die punches may be such as to effect actual perforation of the material to create relatively rough edges 65, see FIG. 4, of the projections 60 to enhance the ability of a gloved finger or fingers to grip the tab 38.

Figure 5:
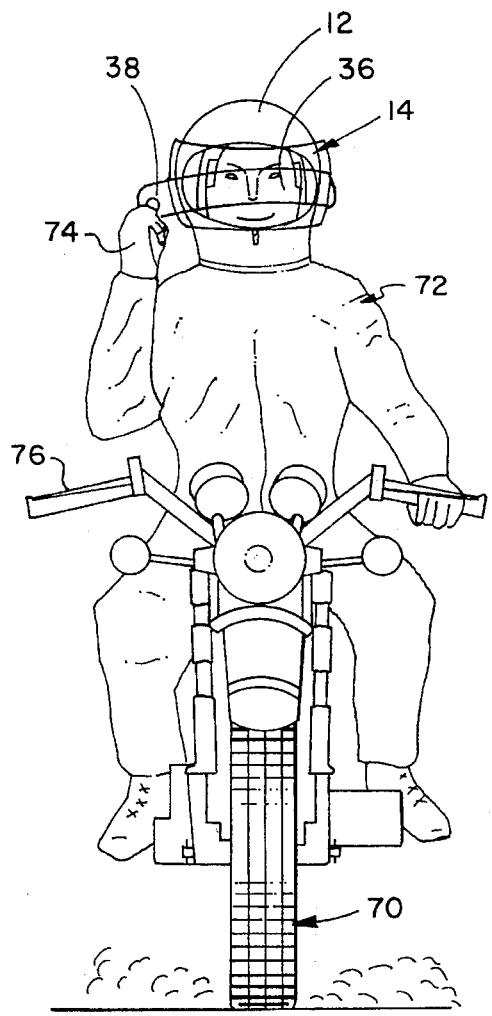
FIG. 5 is a front elevation showing a motorcycle driver using the tear-away lens of the present invention.

Referring briefly to FIG. 5, there is illustrated a race vehicle comprising a motorcycle 70 on which a driver 72 is seated and wearing the helmet 10. When the face shield 14 becomes contaminated to the point of reducing the vision of the driver 72, he or she may reach up quickly with one hand or the other, depending on which side the tab 38 is disposed with respect to the helmet 10, grasp the tab 38 with the thumb and forefinger of the hand 74 and quickly snap the outermost lens 36 off of the shield 14, revealing a clean lens 36 underneath. Those skilled in the art will recognize that the lenses 36 may be stacked on the shield 14 with the tabs 38 disposed on the rider's left side rather than right side if the rider finds it more convenient to remove the left hand from the vehicle steering mechanism, such as the handlebars 76.

The surface interruptions provided on the tab 38 by the projections 60 substantially enhance the ability of a wearer of the helmet 10, having the lenses 36 supported thereon, to quickly remove a lens, when desired. The smooth surfaces of the material of the lens 36 and the tendency for the tab 38 to flap or flutter about in the wind when the vehicle is traveling at high speed reduces the ability of the user to grasp the tab 38. However, thanks to the provision of the projections 60 a lens 36 may be quickly torn away exposing a clean lens underneath whose tab 38 also will assume the position shown in FIG. 2 for the tab of the outermost lens.

FIG. 2 illustrates how multiple lenses 36 may be stacked on the face shield 14 secured to the posts 22 and 24, as shown by way of example for the post 24 in FIG. 2. Each lens 36 is secured on the post 22 and 24 by deflecting the lens material around the respective fastener receiving holes 56 and 58 to secure the lenses on the posts. Each tab 38 is then folded over along the fold line 52 so that the post 24, may easily project through the hole 40. The next lens is then stacked on top of the lens previously mounted on the posts 22 and 24 and the tab 38 of the lens underneath is secured in the folded position by the next or outermost lens. Alternatively, the posts are removed from their base portions and the lenses mounted on the hubs of each post, and the posts are then snapped back on the shield 14. Multiple lenses 36 of sufficient width may be attached directly to the helmet body 11 if a face shield is not required or provided.

Accordingly, as a lens 36 is torn away from the shield 14, the tab 38 of the next or outermost lens 36 will tend to spring back toward a generally planar position thanks to the elastic memory of the lens material and at least assume a position similar to that shown in FIG. 2. In this way, the tab 38 may be easily engaged by the thumb and/or forefinger of a person wearing the lenses on a helmet, such as the helmet 10, permitting easy tear-away of the outermost lens and exposing the next lens and wherein the next lens then has its tab 38 operable to be deflected toward the position shown in FIG. 2. The tabs 38 may be folded in either direction with respect to the projections 60, depending on the preference of the rider. Typically, the projections 60 extend from the inner facing surface 39a of the outermost lens, since it will likely be grasped by the thumb of the person wearing the helmet as he or she reaches up to grasp the tab 38.

Another advantage of the tab 38 resides in the reduced diameter of the arcuate distal end portion 38a, which is preferably less than the transverse width W of the main body 41 of the lens 36, FIG. 3, to reduce the wind resistance of the tab and a tendency to be deflected rearwardly alongside the helmet 10 during high speed racing activity.

The projections 60 are exemplary of a surface interruption of the opposed surfaces 39a and 39b of the tab 38. Other configurations of surface interruption may also be provided within the scope of the invention, including elongated ridges which may be molded, die formed or otherwise provided on the tab 38 or a series of holes punched in the tab 38 in place of the projections 60. Still further, at least the surface 39a of the tab 38 may be provided with a weak adhesive coating which may aid in grasping the tab 38 to tear away a lens 36, when needed or desired.

The construction and use of the lens 36 is believed to be readily understandable by those skilled in the art from the foregoing description. However, briefly, a plurality of lenses 36 may be mounted on the helmet shield 14 by attaching a lens at its mounting opening 58 to the post fastener 22, attaching the other end of the lens 36 to the post fastener 24 at the opening 56, folding the tab 38 at the fold line 52 so that the hole 40 is aligned with the post 24 and the post projects through the hole. Successive lenses 36 are then mounted on the shield 14 in the same manner whereby the outermost lens has its tab 38 substantially free and, due to the elastic memory of the lens material, projecting outwardly away from the helmet 10 as indicated in FIG. 2. As many as five or six lenses may be easily stacked one on top of the other without any reduction in visibility through the stacked lenses. Lesser or greater numbers of lenses may be used, if desired. described in detail, those skilled in the art will recognize that various substitutions and modifications may be made without departing from the scope and spirit of the appended claims.

What is claimed is:

1. A transparent lens for attachment to a face shield and adapted to be quickly removed from said face shield, said face shield having support means thereon for supporting said lens, said lens comprising:

an elongated flexible transparent sheet having means thereon for engaging said support means on said face shield, and a tab at one end of said lens, said tab including surface interruption means formed thereon to provide for gripping said tab to quickly tear said lens away from said face shield, said surface interruption means comprising a plurality of spaced apart projections disposed on said tab add formed by displacing material forming said sheet from at least one surface of said tab to form a roughened surface of said tab.

2. The lens set forth in claim 1 wherein:

said projections include apertures extending through central portions of said projections from one side surface to the other of said sheet to form a roughened edge of said projections, respectively, to aid in grasping said tab.

3. The lens set forth in claim 1 wherein:

said tab includes a grasping hole formed therein and said projections are disposed between said grasping hole and a distal edge of said tab.

4. The lens set forth in claim 1 wherein:

said projections are formed in at least two spaced apart rows adjacent a distal edge of said tab.

5. The lens set forth in claim 1 wherein:

said tab defines an arcuate distal end of said lens having a diameter less than the width of a major portion of said lens.

6. For use in conjunction with a face shield having spaced apart post-like fasteners extending therefrom, a series of adjacent tear-away auxiliary lenses, each comprising:

an elongate, unitary sheet of thin, flexible transparent material defining a central lens body portion and a grasping tab portion;

said central lens body portion having spaced apart fastener receiving holes formed therethrough for receiving the fasteners of the face shield to thereby secure the lens to the face shield;

said tab portion having surface interruption means formed thereon to assist in grasping said tab portion for rapidly tearing said lens away from said face shield, said surface interruption means being formed between a distal edge of said tab portion and a hole formed in said tab portion, add said surface interruption means comprising a plurality of spaced apart projections formed by displacing material forming said lens sheet from at least one surface of said tab portion.

7. The invention set forth in claim 6 wherein:

said projections includes apertures extending through central portion of said projections to form a roughened edge of said projections, respectively.

8. A transparent lens adapted to be supported on a helmet for quick removal from said helmet, said transparent lens comprising:

an elongated flexible sheet having opposed surfaces and a tab formed at one end of said sheet, said tab including a finger grasping hole formed therein and a plurality of projections disposed between said hole and a distal edge of said tab for increasing the surface roughness of said tab to assist in grasping said tab to quickly tear said lens away from said helmet, said projections being formed by displacing the material of said tab away from at least one of said opposed surfaces of said tab, said projections being arranged at plural spaced apart locations between said hole and said distal edge of said tab to assist in grasping said tab by a person wearing said helmet to tear said lens away from said helmet.

9. A transparent lens for attachment to a face shield and adapted to be quickly removed from said face shield, said face shield having spaced apart support means thereon for supporting said lens, said lens comprising:

an elongated flexible transparent sheet having spaced apart openings each comprising a circular hole and a reduced diameter slot extending radially from said hole, each of said slots extending generally toward each other from each of said holes, respectively, for engaging respective ones of said support means on said face shield, and a tab at one end of said lens, said tab including surface interruption means formed thereon to provide for gripping said tab to quickly tear said lens away from said face shield.

* * * * *

UNITED STATES PATENT AND TRADEMARK OFFICE
CERTIFICATE OF CORRECTION

PATENT NO. : 5,592,698
DATED : Jan. 14, 1997
INVENTOR(S) : Marlen M. Woods

It is certified that error appears in the above-identified patent and that said Letters Patent is hereby corrected as shown below:

Col. 6, line 3, change "add" to --- and ---.

Col. 6, line 38, change "add" to --- and ---.

Signed and Sealed this

Twenty-fifth Day of March, 1997

Attest:

BRUCE LEHMAN

Attesting Officer

Commissioner of Patents and Trademarks